(12) United States Patent
Dubief et al.

(10) Patent No.: US 7,211,268 B2
(45) Date of Patent: May 1, 2007

(54) PREPARATION OF POLYSACCHARIDE BETAINATE TYPE COMPOUNDS, COMPOUNDS OBTAINED, THEIR USE AND COMPOSITIONS COMPRISING THEM

(75) Inventors: Claude Dubief, Le Chesnay (FR); Marguerite Rinaudo, Grenoble (FR); Rachel Auzely-Velty, Saint-Georges de Commiers (FR)

(73) Assignee: L'Oreal S.A., Paris (FR)

( * ) Notice: Subject to any disclaimer, the term of this patent is extended or adjusted under 35 U.S.C. 154(b) by 583 days.

(21) Appl. No.: 10/294,685

(22) Filed: Nov. 15, 2002

(65) Prior Publication Data

US 2003/0147818 A1   Aug. 7, 2003

(30) Foreign Application Priority Data

Nov. 15, 2001   (FR)   ................................. 01 14789

(51) Int. Cl.
| | | |
|---|---|---|
| A61Q 19/00 | (2006.01) | |
| A61Q 1/06 | (2006.01) | |
| A61Q 3/00 | (2006.01) | |
| A61Q 5/00 | (2006.01) | |
| A61Q 11/00 | (2006.01) | |

(52) U.S. Cl. ........................... 424/401; 424/49; 424/59; 424/61; 424/62; 424/64; 424/65; 424/69; 424/70.1; 424/70.2; 424/70.6; 424/70.7

(58) Field of Classification Search ..................... None
See application file for complete search history.

(56) References Cited

U.S. PATENT DOCUMENTS

| | | | |
|---|---|---|---|
| 2,047,398 A | 7/1936 | Voss et al. | |
| 2,261,002 A | 10/1941 | Ritter | |
| 2,271,378 A | 1/1942 | Searle | |
| 2,273,780 A | 2/1942 | Dittmar | |
| 2,375,853 A | 5/1945 | Kirby et al. | |
| 2,388,614 A | 11/1945 | Kirby et al. | |
| 2,454,547 A | 11/1948 | Bock et al. | |
| 2,528,378 A | 10/1950 | Mannheimer | |
| 2,723,248 A | 10/1955 | Wirght | |
| 2,781,354 A | 2/1957 | Mannheimer | |
| 2,961,347 A | 11/1960 | Floyd | |
| 3,206,462 A | 9/1965 | McCarty | |
| 3,227,615 A | 1/1966 | Korden | |
| 3,632,559 A | 1/1972 | Matter et al. | |
| 3,716,633 A | 2/1973 | Viout et al. | |
| 3,836,537 A | 9/1974 | Boerwinkle et al. | |
| 3,874,870 A | 4/1975 | Green et al. | |
| 3,917,817 A | 11/1975 | Vanlerberghe et al. | |
| 3,929,990 A | 12/1975 | Green et al. | |
| 3,966,904 A | 6/1976 | Green et al. | |
| 3,990,459 A | 11/1976 | Papantoniou | |
| 4,001,432 A | 1/1977 | Green et al. | |
| 4,005,193 A | 1/1977 | Green et al. | |
| 4,013,787 A | 3/1977 | Varlerberghe et al. | |
| 4,025,617 A | 5/1977 | Green et al. | |
| 4,025,627 A | 5/1977 | Green et al. | |
| 4,025,653 A | 5/1977 | Green et al. | |
| 4,026,945 A | 5/1977 | Green et al. | |
| 4,027,020 A | 5/1977 | Green et al. | |
| 4,031,307 A | 6/1977 | DeMartino et al. | |
| 4,076,912 A | 2/1978 | Papantoniou et al. | |
| 4,128,631 A | 12/1978 | Lundmark et al. | |
| 4,131,576 A | 12/1978 | Iovine et al. | |
| 4,137,180 A | 1/1979 | Naik et al. | |
| 4,137,208 A | 1/1979 | Elliott | |
| 4,167,623 A | 9/1979 | Fujita et al. | |
| 4,172,887 A | 10/1979 | Vanlerberghe et al. | |
| 4,277,581 A | 7/1981 | Vanlerberghe et al. | |
| 4,282,203 A | 8/1981 | Jacquet et al. | |
| 4,349,532 A | 9/1982 | Vanlerberghe et al. | |
| 4,591,610 A | 5/1986 | Grollier | |
| 4,608,250 A | 8/1986 | Jacquet et al. | |
| 4,761,273 A | 8/1988 | Grollier et al. | |
| 4,839,166 A | 6/1989 | Grollier et al. | |
| 4,874,554 A | 10/1989 | Lange et al. | |
| 4,957,732 A | 9/1990 | Grollier et al. | |
| 4,996,059 A | 2/1991 | Grollier et al. | |
| 5,009,880 A | 4/1991 | Grollier et al. | |
| 5,135,748 A * | 8/1992 | Ziegler et al. | .............. 424/401 |
| 5,139,037 A | 8/1992 | Grollier et al. | |
| 5,196,189 A | 3/1993 | Jacquet et al. | |
| 6,210,689 B1 * | 4/2001 | Martino et al. | .............. 424/401 |

FOREIGN PATENT DOCUMENTS

EP          0 122 324          10/1984

(Continued)

OTHER PUBLICATIONS

Skin Care and Cosmetic Ingredients Dictionary, pp. 132-133, 254 (1994).*
Patent Abstracts of Japan, vol. 017, No. 142 (C-1038), Mar. 23, 1993, JP 04 312596 A.
Database WPI, Week 198206, Derwent Publications Ltd., London, GB; AN 1982-11563E, XP002207031 & SU 825 542, May 5, 1981.
Patent Abstracts of Japan, vol. 1996, No. 08, Aug. 30, 1996, JP 08 092039 A.
Patent Abstracts of Japan, vol. 2000, No. 04, Aug. 31, 2000, JP 2000 001504 A.

(Continued)

Primary Examiner—Jyothsna Venkat
(74) Attorney, Agent, or Firm—Finnegan, Henderson, Farabow, Garrett & Dunner L.L.P.

(57) ABSTRACT

A process for preparing compounds from the polysaccharide betainate family, novel compounds so obtained, and their use in cosmetics or in dermatology, as well as the compositions, such as cosmetic or dermatological compositions, comprising said novel compounds.

28 Claims, No Drawings

FOREIGN PATENT DOCUMENTS

| | | |
|---|---|---|
| EP | 0 186 507 | 7/1986 |
| EP | 0 337 354 | 10/1989 |
| EP | 0 342 834 | 11/1989 |
| FR | 2 598 611 | 11/1987 |
| GB | 839 805 | 6/1960 |
| WO | WO 00/15669 | 3/2000 |

OTHER PUBLICATIONS

"Encyclopedia of Polymer Science and Engineering," vol. 13, Poly(phenylene Ether) to Radical Polymerization, A Wiley-Interscience Publication, John Wiley & Sons, 1988, pp. 87-162.

E.A. MacGregor et al., "Polymers in Nature," Chapter 6, Polysaccharides, John Wiley & Sons, 1980, pp. 240-328.

Charles Todd et al., "Volatile silicone fluids for cosmetic formulations," Cosmetics and Toiletries, vol. 91, Jan. 1976, pp. 29-32.

"Encyclopedia of Polymer Science and Engineering," vol. 12, Polyesters to Polypeptide Synthesis, A Wiley-Interscience Publication, John Wiley & Sons, 1988, pp. 658-690.

English language Derwent Abstract of FR 1 564 110, Apr. 18, 1969.

English language Derwent Abstract of FR 2 320 330, Mar. 4, 1977.

English language Derwent Abstract of FR 2 336 434, Jul. 22, 1977.

English language Derwent Abstract of FR 2 357 241, Feb. 3, 1978.

English language Derwent Abstract of FR 2 589 476, May 7, 1987.

English language abstract of WO 01/46264, Jun. 28, 2001.

\* cited by examiner

PREPARATION OF POLYSACCHARIDE BETAINATE TYPE COMPOUNDS, COMPOUNDS OBTAINED, THEIR USE AND COMPOSITIONS COMPRISING THEM

Disclosed herein are methods for preparing compounds from the polysaccharide betainate family, novel compounds so obtained, and their use in cosmetics or in dermatology, as well as novel compositions, such as cosmetic or dermatological compositions, comprising said novel compounds.

Certain starch betainates and their derivatives are compounds well known, for example, in the field of paper-manufacturing. It is known, such as from International Patent Application WO-A-00/15669 and the article "Preparation of starch betainate: a novel cationic starch derivative" in 41 Carbohydrate Polymers 277–283 (2000), that potato starch betainates can be synthesized by esterifying hydroxyl groups in the starch with a betainyl chloride. Esterification is carried out in pyridine and 1,4-dioxane at a temperature of about 110° C.

But that synthesis can be difficult to carry out, due to the operating conditions and to the unstable nature of the betaine derivatives employed, which can impair the reaction yield. After a great deal of research, the inventors have developed at least two novel processes for synthesizing starch betainates, which can produce such compounds much more easily in an improved yield. Further, said processes can allow novel compounds from the polysaccharide betainate family to be prepared. These compounds can have at least one property that can be exploited in the cosmetic or dermatological fields.

In one embodiment, a process for preparing compounds of formula (I) as will be defined below is disclosed. In the process, a polysaccharide is reacted with an N,N-dialkylaminocarboxylic acid of formula (II) as will be defined below, in the presence of at least one reaction activator. Then the ester formed is quaterinized using a quaternization agent.

In another embodiment, another process for preparing compounds of formula (I) as will be defined below is disclosed. In the process, a polysaccharide is reacted with a salt of an N,N,N-trialkylammoniocarboxylic acid of formula (III) as will be defined below. This reaction is carried out in a polar aprotic solvent and takes place in the presence of at least one reaction activator.

Further disclosed herein is a compound of formula (I) as will be defined below, excluding compounds of formula (I) in which Y represents a polymeric starch structure, A represents —CH$_2$—, and R1=R2=R3=—CH$_3$.

Further disclosed herein is a composition, such as a cosmetic and/or dermatological composition, comprising at least one compound as defined above in a cosmetically or dermatologically acceptable medium.

Even further disclosed herein is a process for cosmetic treatment of a keratinous support chosen from skin, scalp, hair, eyelashes, eyebrows, nails, and mucous membranes, comprising applying to said keratinous support a composition as defined above.

In one embodiment, the compounds disclosed herein are compounds from the polysaccharide betainate family of formula (I):

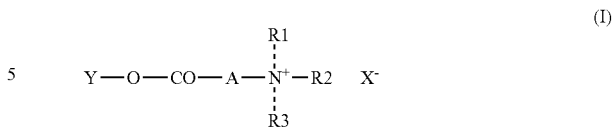

in which:

R$_1$, R$_2$, and R$_3$, which may be identical or different, are chosen from linear and branched, saturated and unsaturated C$_1$–C$_{30}$ hydrocarbon radicals optionally interrupted by at least one heteroatom chosen from N, O, and S and optionally substituted with at least one entity chosen from —OH, halogen atoms (such as chlorine, bromine and iodine) and C$_6$–C$_{22}$ aryl radicals;

A is chosen from linear and branched, saturated and unsaturated divalent C$_1$–C$_{22}$ hydrocarbon radicals, optionally interrupted by at least one hetero atom chosen from N, O, and S and optionally substituted with at least one hydroxyl radical;

X$^-$ is an anion derived from an acid chosen from mineral and organic acids; and Y is a polysaccharide residue;

excluding compounds of formula (I) in which Y represents a polymeric starch structure, A is —CH$_2$—, and R1=R2=R3=—CH$_3$.

For example, R1, R2, and R3, which may be identical or different, are chosen from linear and branched, saturated C$_1$–C$_{14}$ hydrocarbon radicals, such as C$_2$–C$_{12}$ radicals, further such as a methyl radical.

In one embodiment, R1, R2, and R3 are identical and can, for example, be chosen from linear and branched saturated C$_1$–C$_{14}$ hydrocarbon radicals, such as a methyl radical.

In another embodiment, A is chosen from linear and branched saturated divalent C$_1$–C$_4$ hydrocarbon radicals, such as methylene, ethylene, propylene and butylene, and further such as methylene.

Anions derived from an organic acid include, but are not limited to, citrates, lactates, and tartrates. Anions derived from a mineral acid include, but are not limited to, chlorides, bromides, iodides, and sulphates. For example, said anions are chlorides.

The polysaccharides can be chosen from natural and modified polysaccharides. Natural polysaccharides include starches, e.g., starches from vegetable origins such as maize, potato, oats, rice, tapioca, sorghum, barley and wheat; polysaccharides from seed gums such as guar, tara, carob, psyllium, linseed, okra, tamarind, quince gums; polysaccharides from microbial gums such as curdlan, pullulan, dextran, grifolan, schizophyllan, spirulinan, krestin, xanthan, scleroglucan, gellan, succinoglycan gums; polyfructoses such as inulin and levan; algae extracts (agar, alginate, caragheenans, fucoidane, furcellerane, laminarane); extracts from plant exudates (gum arabic, ghatti gum, karaya gum, adraganth gum); celluloses; and chitins.

Modified polysaccharides means polymers obtained by hydrolysis, esterification, etherification, amidation, oxidation, reduction, modification of the hydroxyl groups, covalent incorporation of organometallic residues, grafting, N-acylation, N-alkylation, deamination, or any other modification of the nitrogen-containing functions of polysaccharides containing said functions and/or halogenation using processes known in the art.

Examples of appropriate processes include:
(a) partial hydrolysis of polysaccharide chains using enzymatic treatment, heat treatment, acid treatment or oxidizing treatment;
(b) partial or complete hydrolysis of naturally present ester functions;
(c) partial or complete esterification and/or amidation of naturally present carboxylic functions;
(d) carboxylation using, for example, monochloroacetate;
(e) oxidation of hydroxyl functions in the polysaccharide;
(f) polyoxyalkylenation;
(g) hydrophobic modification of a polysaccharide, for example by reacting a $C_1$–$C_{22}$ alkylating agent such as methyl chloride or nonyl chloride on alkali cellulose or on hydroxyethyl cellulose;
(h) crosslinking of polysaccharide chains; and
(i) grafting, for example, resulting in introducing into the molecule moieties such as polydimethylsiloxane, polyacrylic acid or polymethacrylic acid, polyacrylamide, polymethacrylamide, polyacrylonitrile, sodium polystyrene sulphonate, polyvinylpyrrolidone, polyhydroxyalkyl (meth)acrylate, or the sodium salt of poly(2-acrylamido-2-methylpropanesulphonic) acid.

Modified polysaccharides include hydroxyalkyl celluloses, such as hydroxyethyl celluloses, hydroxyalkyl guars such as hydroxypropyl guar, carboxyalkyl celluloses, carboxyalkyl starches, modified and unmodified chitosans, maltodextrins and cyclodextrins.

The novel compounds can be prepared using one of the following processes as disclosed herein.

In one embodiment, a preparation process ("the first preparation process") is disclosed, comprising:
(i) reacting a polysaccharide with an N,N-dialkylaminocarboxylic acid of formula (II):

in the presence of at least one reaction activator; and (ii) quaternizing the ester formed using a quaternization agent to fix the radical $R_2$ to the nitrogen atom.

In accordance with this process, in (i), a polysaccharide (N,N-dialkylamino)ester is formed. Quarternization of this ester results in the production of the polysaccharide N,N,N-trialkylaminoester salt in (ii).

In one embodiment, the reaction between the polysaccharide and the acid is carried out in a suitable solvent.

In another embodiment, the polysaccharide and the N,N-dialkylaminocarboxylic acid are dissolved or dispersed in said suitable solvent prior to said reaction.

Further in another embodiment, the polysaccharide and the N,N-dialkylaminocarboxylic acid are dissolved or dispersed in said suitable solvent prior to adding the reaction activator The solvent is, for example, polar and aprotic. The solvent can, for example, be chosen from at least one of dimethylsulphoxide (DMSO) and dimethylformamide.

The reaction activator can, for example, be chosen from carbodiimides such as N,N'-diisopropylcarbodiimide; hydroxybenzotriazole, 4-dimethylaminopyridine, and mixtures thereof.

Also, the reaction is, for example, carried out at ambient temperature.

The quaternization agent used can be any quaternization agent known to the skilled person. This agent can, for example, be a halide such as a chloride, an iodide and a bromide, such as a $C_1$–$C_{30}$ alkyl halide, and a sulphate, such as a $C_1$–$C_{30}$ alkyl sulphate. In one embodiment, the quaternization agent is chosen from methyl iodide (MeI) and methyl sulphate ($Me_2SO_4$).

Quaternization is, for example, carried out at a temperature ranging from about 20° C. to about 70° C., such as from about 22° C. to about 27° C.

Quaternization can be carried out with an isolated compound and/or in another solvent medium that differs from the reaction solvent.

Another preparation process ("the second preparation process") comprises reacting a polysaccharide with a salt of an N,N,N-trialkylammoniocarboxylic acid of formula (III):

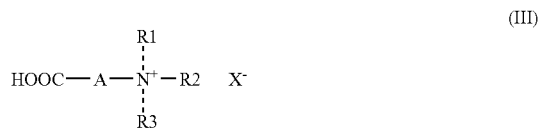

wherein the reaction is carried out in a polar aprotic solvent; and the reaction takes place in the presence of at least one reaction activator.

In one embodiment, the polysaccharide and the acid salt are dissolved or dispersed in the polar aprotic solvent prior to the reaction.

The polar aprotic solvent is, for example, chosen from dimethylsulphoxide (DMSO) and dimethylformamide.

In another embodiment, the polysaccharide and the acid salt are dissolved or dispersed in the solvent prior to adding the reaction activator.

The reaction activator is, for example, chosen from carbodiimides such as N,N'-diisopropylcarbodiimide; hydroxybenzotriazole, 4-dimethylaminopyridine, and mixtures thereof.

This reaction is, for example, carried out at ambient temperature. This reaction is carried out for a period of time, such as from about 3 to 24 hours.

Polysaccharides that can be used in one of those processes are similar to those described above.

Examples of N,N-dialkylaminocarboxylic acids that can be used in the first preparation process include N,N-dimethylglycine (or N,N-dimethylaminoacetic acid), N,N-dimethyl-β-aminopropanoic acid, N,N-dimethyl-γ-aminobutanoic acid, N,N-dimethyl-5-aminopentanoic acid and N,N-dimethylbenzylaminocarboxylic acid. For example, the N,N-dialkylaminocarboxylic acid is N,N-dimethylglycine.

Examples of N,N,N-trialkylammoniocarboxylic acid salts that can be used in the second preparation process include salts of N,N,N-trimethylammonioacetic acid (or N,N,N-trimethylglycine), N,N,N-trimethyl-β-ammoniopropanoic acid, N,N,N-trimethyl-γ-ammoniobutanoic acid, N,N,N-trimethyl-5-ammoniopentanoic acid, and N,N,N-trimethylbenzylammoniocarboxylic acid.

These salts can be derived from an acid chosen from organic acids, for example, citrates, lactates and tartrates, and mineral acids, such as halides (e.g., chlorides, bromides, iodides), and sulphates. In one embodiment, said salts are chlorides. The chloride of N,N,N-trimethylammonioacetic acid, also known as betainyl chloride, can also be used.

The two preparation processes described above can further comprise at least one subsequent option, such as anion exchange or purification, for example, ultrafiltration.

The novel compounds disclosed herein can be present in the cosmetic or dermatological compositions in a concentration ranging, for example, from about 0.01% to about 20% by weight relative to the total weight of the composition, such as from about 0.05% to about 15% by weight, and further such as from about 0.1% to about 10% by weight relative to the total weight of the composition.

The cosmetic or dermatological compositions disclosed herein comprise a cosmetically or dermatologically acceptable medium, i.e., a medium that is compatible with application to a keratinous substance such as skin, scalp, mucous membranes, nails, eyelashes, eyebrows, body, head hair or any other cutaneous zone of face or body.

The pH of said composition is ranging, for example, from about 1 to about 13, such as from about 2 to about 12.

The cosmetically or dermatologically acceptable medium can comprise water and/or at least one organic solvent chosen from cosmetically and dermatologically acceptable organic solvents. The at least one organic solvent can be in an amount ranging from about 1% to about 98% by weight relative to the total weight of the composition. The at least one organic solvent can be chosen from hydrophilic organic solvents, lipophilic organic solvents, and amphiphilic organic solvents.

Hydrophilic organic solvents that can be used are chosen, for example, from linear and branched monoalcohols comprising from 1 to 8 carbon atoms, such as ethanol, propanol, butanol, isopropanol and isobutanol; polyethylene glycols comprising from about 6 to about 80 mol of ethylene oxide; polyols such as propylene glycol, butylene glycol, glycerol and sorbitol; mono- and dialkyl isosorbide with alkyl groups that comprise from 1 to 5 carbon atoms such as dimethyl isosorbide; glycol ethers such as diethylene glycol monomethyl ether and diethylene glycol monoethyl ether; and propylene glycol ethers such as dipropylene glycol methyl ether.

Lipophilic organic solvents that can be used include liquid fatty esters such as diisopropyl adipate, dioctyl adipate, and alkyl benzoates.

Amphiphilic organic solvents that can be used include polyols such as derivatives of polypropylene glycol (PPG), for example, esters of polypropylene glycol and fatty acids, and esters of PPG and fatty alcohols such as PPG-23 oleyl ether and PPG-36 oleate.

The compositions can further comprise at least one complementary compound chosen from monosaccharides, oligosaccharides and polysaccharides, which may or may not be hydrolysed, and which may be modified or unmodified, identical or not identical, and different from the novel compounds disclosed herein. Such compounds can, for example, be chosen from those described in the "Encyclopaedia of Polymer Science and Engineering," vol. 13, pp. 87–162 and vol. 12, pp. 658–690, John Wiley & Sons, 2d ed., 1988, and in "Polymers in Nature," by E. A. MacGregor & C. T. Greenwood, John Wiley & Sons, Chapter 6, pp. 240–328, 1980, and in "Industrial Gums—Polysaccharides and their Derivatives," edited by Roy L. Whistler (Academic Press Inc., 2d ed.).

These compounds include, but are not limited to, glucanes such as β-glucanes; modified or unmodified starches, such as those from cereals, for example wheat, maize and rice, from vegetables such as white peas, from tubers such as potatoes and cassava; amylase, amylopectin, glycogen, dextrans; celluloses and their derivatives such as methyl celluloses, hydroxyalkyl celluloses, ethylhydroxyethyl celluloses, carboxymethyl celluloses, fructosans, inulin, levan, mannans, xylans, lignins, arabans, galactans, galacturonans; chitin, chitosans and derivatives thereof; glucoronoxylans, arabinoxylans, xyloglucans; glucomannans; pectic acids and pectins; alginic acid and alginates; arabinogalactans, carragheenans, agars, glycosaminoglucans, gum arabics, tragacanth gums, ghatti gums, karaya gums, carob gums, xanthan gums, cyclodextrins, and mixtures thereof.

The novel compositions can also comprise at least one complementary compound chosen from amino acids, oligopeptides, peptides and proteins, which may or may not be hydrolysed, and which may be modified or unmodified. These amino acids can include, for example, cysteine, lysine, alanine, N-phenylalanine, arginine, glycine, leucine, and mixtures thereof. Examples of oligopeptides, peptides or proteins, which may or may not be hydrolysed, and which may be modified or unmodified include modified or unmodified hydrolysates or wool or silk proteins, and vegetable proteins such as wheat proteins.

The novel compositions can comprise at least one complementary compound chosen from branched and unbranched fatty alcohols and acids. Suitable fatty acids include, for example, $C_8$–$C_{30}$ carboxylic acids such as palmitic acid, oleic acid, linoleic acid, myristic acid, stearic acid, lauric acid, and mixtures thereof. Suitable fatty alcohols include, for example, $C_8$–$C_{30}$ alcohols such as palmitylic alcohol, oleic alcohol, linoleyl alcohol, myristyl alcohol, stearyl alcohol, lauryl alcohol, and mixtures thereof.

Also, the novel compositions can comprise at least one complementary compound chosen from waxes of animal, vegetable, and mineral origin. As used herein, the term "wax" means a lipophilic compound that is a solid at ambient temperature (about 25° C.), with a reversible solid/liquid change of state and with a melting point of more than about 40° C. and up to about 200° C., and having an anisotropic crystalline organization in the solid state. In general, the size of the wax crystals is such that the crystals diffract and/or diffuse light, endowing the composition comprising it with a cloudy, more or less opaque appearance. Heating the wax to its melting point renders it miscible with oils to form a microscopically homogeneous mixture, but cooling the temperature of the mixture to ambient temperature causes the wax to recrystallize in the oils of the mixture, which is detected microscopically and macroscopically (opalescence).

Suitable waxes include waxes of animal origin such as beeswax, spermaceti, lanolin wax, and lanolin derivatives; waxes of vegetable origin such as carnauba wax, candelilla wax, ouricury wax, Japan wax, cocoa butter or waxes from cork fibres and sugarcane; and waxes of mineral origin such as paraffin waxes, vaseline waxes, lignite waxes, microcrystalline waxes, ozokerites, and mixtures thereof.

The compositions can also comprise at least one complementary compound chosen from ceramides and pseudoceramides. Examples include ceramides in classes I, II, III, and IV according to DOWNING's classification, and mixtures thereof, such as N-oleyldehydrosphingosin.

The compositions can comprise at least one hydroxylated organic acid chosen from acids that are well known and used in the art. For example, citric acid, lactic acid, tartaric acid, malic acid, and mixtures thereof may be used.

Moreover, the compositions can comprise at least one sunscreen chosen from UV-A and UV-B active sunscreens that are known to the skilled person. Examples include dibenzoylmethane derivatives such as 4-methyldibenzoylmethane, 4-isopropyldibenzoylmethane, 4-tert-butyldibenzoylmethane, 2,4-dimethyldibenzoylmethane, 4-tert-butyl-4'-diisopropyldibenzoylmethane, para-aminobenzoic acid and its esters such as 2-ethylhexyl para-dimethylaminobenzoate and ethyl-N-propyloxylated para-aminobenzoate, salicylates such as triethanolamine salicylate, cinnamic acid esters such as 2-ethylhexyl 4-methoxycinnamate, methyl diisopropylcinnamate, methyl anthranilate, benzotriazole derivatives, triazine derivatives, β,β'-diphenylacrylate derivatives such as 2-ethylhexyl 2-cyano-3,3-diphenylacrylate and ethyl 2-cyano-3,3-diphenylacrylate, 2-phenylbenzimidazole-5-sulphonic acid and its salts, benzophenone derivatives, benzylidenecamphor derivatives, silicone filters, and mixtures thereof.

Additionally, compositions can comprise at least one complementary compound chosen from antioxidants and free radical scavengers. Examples include ascorbic acid, ascorbyl compounds such as ascorbyl dipalmitate, t-butylhydroquinone, polyphenols such as phloroglucinol, sodium sulphite, erythorbic acid, flavonoids, and mixtures thereof.

The compositions can also comprise at least one chelating agent chosen from EDTA (ethylenediaminetetraacetic acid) and its salts, such as disodium EDTA and dipotassium EDTA, phosphated compounds such as sodium metaphosphate, sodium hexametaphosphate, tetrapotassium pyrophosphate, phosphonic acids and their salts such as salts of ethylenediaminetetramethylenephosphonic acid, and mixtures thereof.

The compositions can further comprise at least one complementary compound chosen from antifungal and antibacterial agents chosen from the following examples:
(a) benzethonium chloride, benzalkonium chloride, chlorhexidine, chloramine T, chloramine B, 1,3-dibromo-5,5-dimethylhydantoin, 1,3-dichloro-5,5-dimethylhydantoin, 3-bromo-1-chloro-5,5-dimethylhydantoin and N-chlorosuccinimide;
(b) 1-hydroxy-2-pyridone derivatives such as 1-hydroxy-4-methyl-2-pyridone, 1-hydroxy-6-methyl-2-pyridone and 1-hydroxy-4,6-dimethyl-2-pyridone;
(c) trihalogenocarbamides;
(d) triclosan;
(e) azole compounds such as climbazole, ketoconazole, clotrinazole, econazole, isoconazole and miconazole b;
(f) antifungal polymers such as amphotericin B and nystatin;
(g) selenium sulphides;
(h) sulphur in its different forms, cadmium sulphide, allantoin, coal tar and wood tar and their derivatives, such as cade oil, undecylenic acid, fumaric acid, and allylamines such as terbinafine;
(i) and a mixture thereof.

It is also possible to use those agents in the form of the physiologically acceptable acid addition salts thereof, such as in the form of salts of sulphuric acid, nitric acid, thiocyanic acid, hydrochloric acid, hydrobromic acid, hydroiodic acid, phosphoric acid, acetic acid, benzoic acid, glycolic acid, aceturic acid, succinic acid, nicotinic acid, tartaric acid, maleic acid, palmitic acid, methanesulphonic acid, propanoic acid, 2-oxopropanoic acid, propanedioic acid, 2-hydroxy-1,4-butanedioic acid, 3-phenyl-2-propenoic acid, hydroxybenzeneacetic acid, ethanesulphonic acid, 2-hydroxyethanesulphonic acid, 4-methylbenzenesulphonic acid, 4-amino-2-hydroxybenzoic acid, 2-phenoxybenzoic acid, 2-acetyloxybenzoic acid, picric acid, lactic acid, citric acid, malic acid, oxalic acid, and amino acids.

The antifungal or antibacterial acids mentioned above can also be used in the form of their addition salts of physiologically acceptable organic or inorganic bases. Examples of the organic bases include alkanolamines with low molecular weights such as ethanolamine, diethanolamine, N-ethylethanolamine, triethanolamine, diethylaminoethanol, 2-amino-2-methylpropanedione; non-volatile bases such as ethylenediamine, hexamethylenediamine, cyclohexylamine, benzylamine, N-methylpiperazine; quaternary ammonium hydroxides, for example trimethylbenzyl hydroxide; and guanidine and its derivatives, in particular alkyl derivatives. Examples of the inorganic bases include salts of alkali metals such as sodium and potassium; ammonium salts, salts of alkaline-earth metals such as magnesium and calcium; and salts of di-, tri- or tetra-valent cationic metals such as zinc, aluminium and zirconium. Alkanolamines, ethylenediamine and inorganic bases such as alkali metal salts can, for example, be used.

The compositions can additionally comprise at least one dandruff-regulating agent such as succinylchitosan and poly-β-alanine, and mixtures thereof.

The compositions can further comprise at least one thickening agent such as azulene or glycyrrhetinic acid, and mixtures thereof.

Additionally, the compositions can comprise at least one polymer chosen from cationic polymers. Cationic polymer means any polymer chosen from polymers containing at least one cationic group and polymers containing at least one group that is ionizable to a cationic group. Suitable cationic polymers for use can be chosen from any of those that are known to improve the cosmetic properties of hair treated with detergent compositions, such as those described in European patent application EP-A-0 337 354 and in French Patent Applications FR-A-2 270 846, FR-A-2 383 660, FR-A-2 598 611, FR-A-2 470 596, and FR-A-2 519 863. Examples of the cationic polymers include those containing moieties comprising at least one amine group chosen from primary, secondary tertiary and quaternary amine groups, which can either form part of the main polymer chain or be carried by a side substituent bonded directly to the main polymer chain.

The cationic polymers used generally have a number average molecular mass in the range from about 500 to about $5 \times 10^6$, such as in the range from about $10^3$ to about $3 \times 10^6$. These cationic polymers include polymers of the polyamine, polyaminoamide, and quaternary polyammonium type, such as those described in French Patents FR-A-2 505 348 and FR-A-2 542 997. The described cationic polymers are chosen, for example, from:
(1) homopolymers and copolymers derived from acrylic acid or methacrylic acid esters or amides;
(2) cellulose ether derivatives comprising quaternary ammonium groups described in French Patent FR-A-1 492 597;
(3) cationic cellulose derivatives such as cellulose copolymers or cellulose derivatives grafted with a hydrosoluble quaternary ammonium monomer and as is described in U.S. Pat. No. 4,131,576, such as hydroxyalkyl celluloses, for example hydroxymethyl, hydroxyethyl or hydroxypropyl celluloses grafted, for example, with a salt chosen from methacryloylethyltrimethylammonium salts, methacrylamidopropyltrimethylammonium salts and dimethyldiallylammonium salts;
(4) cationic polysaccharides, such as those described in U.S. Pat. Nos. 3,589,578 and 4,031,307, such as guar gums containing cationic trialkylammonium groups;
(5) polymers comprising piperazinyl moieties and divalent alkylene or hydroxyalkylene groups with linear or branched chains, optionally interrupted by at least one atom chosen from oxygen, sulphur, and nitrogen atoms or by at least one ring chosen from aromatic and heterocyclic rings, and the at least one of the oxidation and quaternization products of said polymers. Such polymers have been described, for example, in French Patent Nos. 2 162 025 and 2 280 361;

(6) water-soluble polyaminoamides such as those described in French Patent Nos. 2 252 840 and 2 368 508;

(7) polyaminoamide derivatives, for example adipic acid/dialkylaminohydroxyalkyldialkylene-triamine polymers in which the alkyl group comprises from 1 to 4 carbon atoms and such as a methyl, ethyl or propyl group, and the alkylene group comprises from 1 to 4 carbon atoms and such as an ethylene group. Such polymers have been described, for example, in French Patent No. 1 583 363;

(8) polymers obtained by reacting a polyalkylene-polyamine containing two primary amine groups and at least one secondary amine group, with a dibasic carboxylic acid selected from diglycolic acids and saturated aliphatic dibasic carboxylic acids comprising from 3 to 8 carbon atoms. The molar ratio between the polyalkylene-polyamine and the dibasic carboxylic acid is in the range from about 0.8:1 to about 1.4:1; the resulting polyaminoamide may be reacted with epichlorhydrin in a molar ratio of epichlorhydrin to the secondary amine group of the polyaminoamide in the range from about 0.5:1 to about 1.8:1. Such polymers have been described, for example, in U.S. Pat. Nos. 3,227,615 and 2,961,347;

(9) alkyldiallylamine and dialkyldiallylammonium cyclopolymers such as homopolymer of dimethyldiallylammonium chloride and copolymers of diallyldimethylammonium chloride and acrylamide;

(10) quaternary di-ammonium polymers with a number average molar mass that is generally in the range from about 1000 to about 100,000, such as those described, for example, in French Patents FR-A-2 320 330, FR-A-2 270 846, FR-A-2 316 271, FR-A-2 336 434 and FR-A-2 413 907 and in U.S. Pat. Nos. 2,273,780, 2,378,853, 2,388, 614, 2,454,547, 3,206,462, 2,261,002, 2,271,378, 3,874, 870, 4,001,432, 3,929,990, 3,966,904, 4,005,193, 4,025, 617, 4,025,627, 4,025,653, 4,026,945, 4,027,020;

(11) quaternary polyammonium polymers such as those described in European Patent application EP-A-0 122 324;

(12) quaternary polymers of vinylpyrrolidone and vinylimidazole such as those sold by BASF under the trade names Luviquat® FC 905, FC 550 and FC 370;

(13) polyamines such as Polyquart® H sold by COGNIS, referred to as "POLYETHYLENEGLYCOL (15) TALLOW POLYAMINE" in the CTFA dictionary;

(14) crosslinked polymers of methacryloyloxy($C_1$–$C_4$)alkyl ($C_1$–$C_4$)trialkylammonium salts such as those sold by ALLIED COLLOIDS under the trade name SALCARE® SC 92, SALCARE® SC 95 and SALCARE® SC 96; and

(15) mixtures thereof.

Other cationic polymers that can be used are chosen, for example, from cationic proteins and hydrolysates of cationic proteins, polyalkyleneimines, such as polyethyleneimines, polymers comprising moieties chosen from vinylpyridine and vinylpyridinium moieties, condensates of polyamines and epichlorhydrin, quaternary polyureylenes, and chitin derivatives.

Of the cationic polymers mentioned above, quaternary cellulose ether derivatives, cationic cyclopolymers, quaternary polymers of vinylpyrrolidone and vinylimidazole and mixtures thereof can, for example, be used.

The compositions can comprise at least one polymer chosen from amphoteric polymers. Amphoteric polymers that can be used can be chosen from polymers comprising moieties B and C statistically distributed in the polymer chain, wherein B is a moiety deriving from a monomer comprising at least one basic nitrogen atom and C is a moiety deriving from an acid monomer comprising at least one group chosen from carboxylic and sulphonic groups, or B and C can be groups deriving from zwitterionic monomers of carboxybetaines or sulphobetaines; B and C can also be a cationic polymer chain comprising at least one amine group chosen from primary, secondary, tertiary and quaternary amine groups in which at least one of the amine groups carries a carboxylic or sulphonic group bonded via a hydrocarbon group, or B and C form part of a chain of a polymer with an ethylene-$\alpha\beta$-dicarboxylic moiety wherein one of the carboxylic groups has been reacted with a polyamine containing at least one amine group chosen from primary and secondary amine groups.

The amphoteric polymers can, for example, be chosen from the following polymers:

(1) polymers resulting from copolymerization of at least one monomer derived from a vinyl compound carrying a carboxylic group, such as acrylic acid, methacrylic acid, maleic acid, and alpha-chloracrylic acid, and at least one basic monomer derived from a substituted vinyl compound comprising at least one basic atom, such as dialkylaminoalkyl methacrylate and acrylate, dialkylaminoalkyl methacrylamide, and -acrylamide. Such compounds have been described, for example, in U.S. Pat. No. 3,836,537. The sodium acrylate/acrylamidopropyltrimethylammonium chloride copolymer sold by COGNIS as POLYQUART® KE 3033 can, for example, be used. The vinyl compound can also be a dialkyldiallylammonium salt such as diethyldiallylammonium chloride. Copolymers of acrylic acid and of the latter monomer have been produced by CALGON under the trade names MERQUAT® 280, MERQUAT® 295, and MERQUAT® PLUS 3330;

(2) polymers comprising moieties deriving from:
  (a) at least one monomer selected from acrylamides or methacrylamides substituted on the nitrogen atom with an alkyl group;
  (b) at least one acidic comonomer comprising at least one reactive carboxylic group; and
  (c) at least one basic comonomer such as esters with substituents chosen from primary, secondary, tertiary and quaternary amine substituents of acrylic and methacrylic acids and the quaternization product of dimethylaminoethyl methacrylate with dimethyl or diethyl sulphate.

In one embodiment, N-substituted acrylamides or methacrylamides are groups wherein the alkyl groups comprise from 2 to 12 carbon atoms, such as N-ethylacrylamide, N-tertiobutylacrylamide, N-tertiooctylacrylamide, N-octylacrylamide, N-decylacrylamide, N-dodecylacrylamide, and corresponding methacrylamides.

The acidic comonomers can be chosen, for example, from acrylic, methacrylic, crotonic, itaconic, maleic, and fumaric acids, as well as alkyl monoesters comprising from 1 to 4 carbon atoms of the maleic or fumaric acids or anhydrides. The basic comonomers are chosen, for example, from aminoethyl, butylaminoethyl, N,N'-dimethylaminoethyl, and N-tertiobutylaminoethyl methacrylates. The copolymers with the CTFA designation (4th ed., 1991) "Octylacrylamide/acrylates/butylaminoethyl-methacrylate copolymer" such as products sold by NATIONAL STARCH under the trade name AMPHOMER® or LOVOCRYL® 47 can be used.

(3) crosslinked and partially or completely alkylated polyaminoamides derived from polyaminoamides of the general formula:

  (IV)

in which $R_{10}$ is a divalent group derived from saturated dibasic carboxylic acid, mono- and dibasic carboxylic acids comprising an ethylenic double bond, an ester of an alkanol comprising from 1 to 6 carbon atoms of said acids and a group derived from addition of any one of said acids with amines chosen from bis-primary or bis-secondary amines, and Z is a group chosen from bis-primary, mono- and bis-secondary polyalkylene-polyamine groups, and, for example, Z represents:

(a) in proportions of from about 60 to about 100 mol %, the group:

  (V)

in which x=2 and p=2 or 3, or x=3 and p=2; this group being derived from a compound chosen from diethylenetriamine, triethylenetetraamine and dipropylenetriamine;

(b) in proportions of from 0 to about 40 mol %, the group (V) above, in which x=2 and p=1 and which is derived from a compound chosen from ethylenediamine and piperazine:

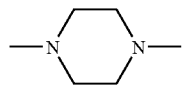

(c) in proportions of from 0 to about 20% by weight, the group $-NH-(CH_2)_6-NH-$, which is derived from hexamethylenediamine, said polyaminoamines being crosslinked by adding a bifunctional crosslinking agent chosen from epihalohydrins, diepoxides, dianhydrides, and bis-unsaturated derivatives, in an amount of from about 0.025 to about 0.35 mol of crosslinking agent per amine group of the polyaminoamide and alkylated by the action of acrylic acid, chloroacetic acid or an alkane-sultone or salts thereof.

In one embodiment, the saturated carboxylic acids are, for example, chosen from acids comprising from 6 to 10 carbon atoms such as the adipic acid 2,2,4-trimethyladipic acid and 2,4,4-trimethyladipic acid, terephthalic acid, and acids comprising a double ethylenic bond such as acrylic acid, methacrylic acid, and itaconic acid. The alkane-sultones used in the alkylation can be chosen, for example, from propane- and butane-sultones; the alkylation agent salts can be chosen, for example, from sodium and potassium salts.

(4) polymers comprising zwitterionic moieties with formula:

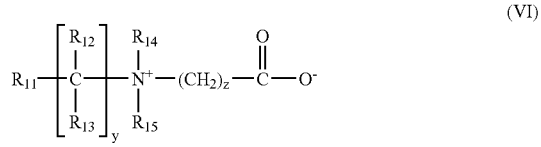  (VI)

in which $R_{11}$ is chosen from polymerizable unsaturated groups such as an acrylate, methacrylate, acrylamide and methacrylamide groups, y and z, which may be identical or different, are chosen from integers from 1 to 3, $R_{12}$ and $R_{13}$, which may be identical or different, are chosen from a hydrogen atom, methyl, ethyl and propyl groups, and $R_{14}$ and $R_{15}$, which may be identical or different, are chosen from a hydrogen atom and alkyl groups so that the sum of the carbon atoms in $R_{14}$ and $R_{15}$ does not exceed 10.

Polymers comprising such moieties can also comprise moieties derived from non-zwitterionic monomers such as monomers chosen from dimethyl- and diethylaminoethyl acrylates and methacrylates, alkyl acrylates and methacrylates, acrylamides, methacrylamides, and vinyl acetate. By way of example, mention may be made of the copolymer of methyl methacrylate and methyl dimethylcarboxymethylammonioethylmethacrylate, such as the product sold by SANDOZ as DIAFORMER® Z301.

(5) polymers derived from chitosan comprising monomer moieties with the following formulae:

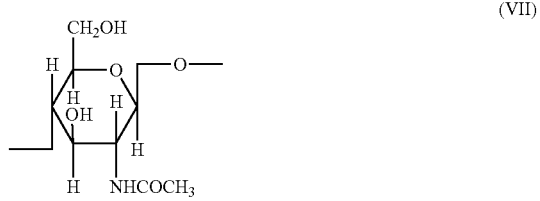  (VII)

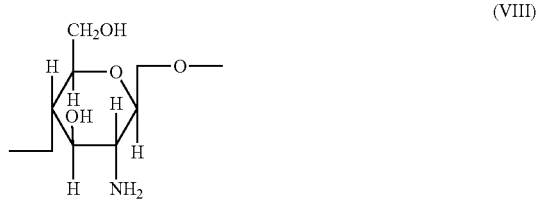  (VIII)

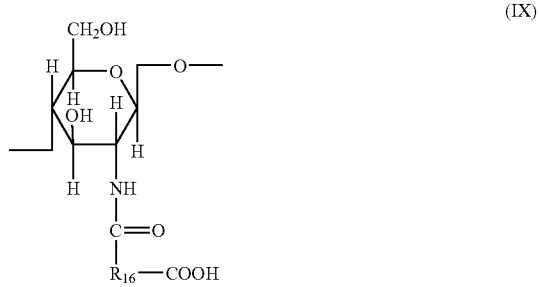  (IX)

the moiety (VII) being present in proportions in the range from 0 to about 30%, the moiety (VIII) in proportions in the range from about 5% to about 50%, and the moiety (IX) in proportions in the range from about 30% to about 90%, it being understood that in said moiety (IX), $R_{16}$ is a group with the formula:

  (X)

in which q is equal to 0 or 1;

if q=0, $R_{17}$, $R_{18}$, and $R_{19}$, which may be identical or different, are chosen from a hydrogen atom, methyl, hydroxyl, acetoxy and amino residues, monoalkylamine residues and dialkylamine residues optionally interrupted by at least one nitrogen atom and/or optionally substituted with at least one group chosen from amine, hydroxyl, carboxyl, alkylthio and sulphonic groups, and alkylthio residues in which the alkyl group carries an amino residue, wherein at least one of groups $R_{17}$, $R_{18}$, and $R_{19}$ in this case is a hydrogen atom; or if q=1, $R_{17}$, $R_{18}$, and $R_{19}$, which may be identical or different, are each chosen from a hydrogen atom, and salts formed by said compounds with bases or acids.

(6) polymers derived from N-carboxyalkylation of chitosan such as N-carboxymethylchitosan and N-carboxybutyl-chitosan sold by JAN DEKKER under the trade name EVALSAN®.

(7) polymers corresponding to the general formula (XI) described, for example, in French Patent No. 1 400 366:

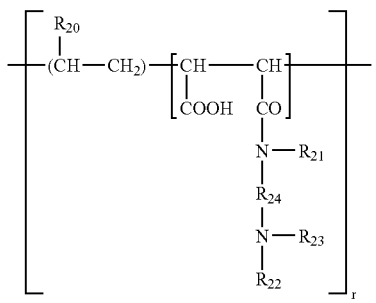

(XI)

in which $R_{20}$ is chosen from a hydrogen atom, $CH_3O$, $CH_3CH_2O$ and phenyl groups, $R_{21}$ is chosen from hydrogen and lower alkyl groups such as methyl and ethyl, $R_{22}$ is chosen from hydrogen and lower alkyl groups such as methyl and ethyl, $R_{23}$ is chosen from lower alkyl groups such as methyl and ethyl groups and groups with the formula: $-R_{24}-N(R_{22})_2$, wherein $R_{24}$ is chosen from groups of $-CH_2-CH_2-$, $-CH_2-CH_2-CH_2-$, and $-CH_2-CH(CH_3)-$, and $R_{22}$ is chosen from hydrogen and lower alkyl groups such as methyl and ethyl; and higher homologues of said groups comprising up to 6 carbon atoms.

(8) amphoteric polymers of the type —D—X—D—X— chosen from:

(a) polymers obtained by the action of chloroacetic acid or sodium chloroacetate on compounds comprising at least one moiety corresponding to the formula:

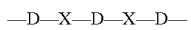  (XII)

in which D is a group:

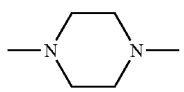

and X is chosen from the symbols E and E', wherein E and E', which may be identical or different, are chosen from alkylene groups with at least one chain chosen from straight and branched chains comprising from 1 to 7 carbon atoms in its main chain, wherein said alkylene groups are unsubstituted or substituted with at least one hydroxyl group. E or E' can optionally also comprise at least one atom chosen from oxygen, nitrogen and sulphur atoms, and 1 to 3 rings chosen from aromatic and heterocyclic cycles. The oxygen, nitrogen, and sulphur atoms can be present in the form of at least one group chosen from ether, thioether, sulphoxide, sulphone, sulphonium, alkylamine, alkenylamine, hydroxyl, benzylamine, amine oxide, quaternary ammonium, amide, imide, alcohol, ester and urethane groups.

(b) polymers corresponding to the formula:

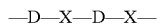  (XIII)

in which D is a group:

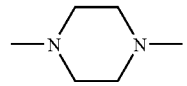

and X is chosen from the symbols E and E', and wherein at least one X is chosen from E'; E having the meaning given above and E' being a divalent alkylene group with at least one chain chosen from straight and branched chains comprising from 1 to –7 carbon atoms in the main chain, wherein said divalent alkylene group is unsubstituted or substituted with at least one hydroxyl group and comprises at least one nitrogen atom, the nitrogen atom being substituted with an alkyl chain which is optionally interrupted by an oxygen atom, wherein said alkyl chain comprises at least one functional group chosen from carboxyl functional groups and hydroxyl functional groups and wherein said alkyl chain is betainized by reaction with a reactant chosen from chloroacetic acid and sodium chloroacetate.

(9) alkyl($C_1$–$C_5$)vinyl ether/maleic anhydride copolymers partially modified by semiamidation with an N,N-dialkylaminoalkylamine such as N,N-dimethylaminopropylamine or by semi-esterification with an N,N-dialkanolamine. These copolymers can also comprise other vinyl compounds such as vinylcaprolactam.

In one embodiment, the amphoteric polymers are chosen from polymers of family (1).

Additionally, the compositions can comprise at least one polymer chosen from anionic polymers, which are either soluble or dispersed. Examples of the anionic polymers are chosen from polymers comprising carboxylic, sulphonic and phosphoric groups, and can have a mass average or number average molecular mass in the range from about 500 to about 5,000,000.

The carboxylic groups are derived from unsaturated monoacidic or dibasic carboxylic acid monomers, such as those corresponding to the following formula:

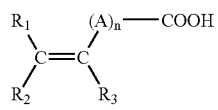  (XIV)

In which:

n is an integer ranging from 0 to 10;

A is a methylene group, optionally bonded to the carbon atom of the unsaturated group or to the neighbouring methylene group when n is greater than 1 via a hetero atom such as oxygen or sulphur;

$R_1$ is chosen from a hydrogen atom, and phenyl and benzyl groups;

$R_2$ is chosen from a hydrogen atom, alkyl groups comprising from 1 to 6 carbon atoms and carboxyl groups; and $R_3$ is chosen from a hydrogen atom, alkyl groups comprising from 1 to 6 carbon atoms, and —$CH_2$—COOH, phenyl and benzyl groups.

In formula (XIV) above, the alkyl groups comprise, for example, from 1 to 4 carbon atoms, such as methyl and ethyl groups.

The anionic polymers with carboxylic groups are chosen, for example, from:

A) homo- and copolymers of acrylic and methacrylic acid and their salts, such as products sold by ALLIED COLLOID under the trade name VERSICOL® E or K, or by BASF under the trade name ULTRAHOLD®, and acrylic acid and acrylamide copolymers sold by HERCULES in the form of their sodium salt under the trade names RETEN® 421, 423 or 425, the sodium salts of polyhydroxycarboxylic acids;

B) copolymers of acrylic and methacrylic acid with a monoethylenic monomer such as ethylene, styrene, vinyl esters, acrylic and methacrylic esters, optionally grafted to a polyalkylene glycol, such as polyethylene glycol, and optionally crosslinked. Such polymers have, for example, been described in French Patent FR-A-1 222 944 and German Patent Application DE-A-2 330 956, copolymers of that type comprising in their chain an acrylamide moiety, optionally N-alkylated and/or hydroxyalkylated as described, for example, in Luxembourg Patent Applications L-A-75370 and 75371 or sold by AMERICAN CYANAMID under the trade name QUADRAMER®. Also included are copolymers of acrylic acid and $C_1$–$C_4$ alkyl methacrylate and the copolymer of methacrylic acid and ethyl acrylate sold by BASF as LUVIMER® MAEX.

C) copolymers derived from crotonic acid, such as those comprising vinyl acetate or propionate moieties in their chain, and optionally other monomers such as allyl and methallyl esters, vinyl ethers and vinyl esters of an acid chosen from linear and branched, saturated long-hydrocarbon-chain carboxylic acids such as those containing at least 5 carbon atoms, said polymers optionally being grafted and crosslinked, or a vinyl, allyl and methallyl esters of an α- or β-cyclic carboxylic acid. These polymers have, inter alia, been described in French Patents FR-A-1 222 944, FR-A-1 580 545, FR-A-2 265 782, FR-A-2 265 781, FR-A-1 564 110, and FR-A-2 439 798. Commercially available products included in this class are resins 28-29-30, 26-13-14 and 28-13-10 sold by NATIONAL STARCH.

D) polymers derived from maleic, fumaric or itaconic acids or anhydrides with vinyl esters, vinyl ethers, vinyl halides, phenyl vinyl derivatives, acrylic acid and its esters; said polymers may be esterified. Such polymers have been described, for example, in U.S. Pat. Nos. 2,047,398, 2,723,248, 2,102,113, United Kingdom Patent GB-A-839 805, and include those sold by ISP under the trade names GANTREZ® AN or ES.

Polymers that also fall within this class are copolymers of maleic, citraconic or itaconic anhydrides with an allyl or methallyl ester optionally comprising at least one group chosen from acrylamide, methacrylamide, α-olefin, acrylic and methacrylic esters, acrylic and methacrylic acids and vinylpyrrolidone groups in their chain, the anhydride functions optionally being monoesterified or monoamidified. Such polymers have, for example, been described in French Patents FR-A-2 350 384 and FR-A-2 357 241.

E) Polyacrylamides comprising carboxylate groups.

Polymers comprising sulphonic groups are polymers comprising at least one moiety chosen from vinylsulphonic, styrenesulphonic, naphthalenesulphonic and acrylamidoalkylsulphonic moieties. Said polymers can, for example, be chosen from:

(a) polyvinylsulphonic acid salts with a molar mass in the range from about 1000 to about 100,000 and copolymers with an unsaturated comonomer such as acrylic and methacrylic acid and their esters, as well as acrylamide and its derivatives, vinyl ethers and vinylpyrrolidone;

(b) polystyrenesulphonic acid salts and sodium salts with molecular weights of about 500,000 and about 100,000, respectively, sold by NATIONAL STARCH under the trade names FLEXAN® 500 and FLEXAN® 130. Said compounds have been described in French Patent FR-A-2 198 719;

(c) polyacrylamide-sulphonic acid salts such as those mentioned in U.S. Pat. No. 4,128,631, for example, polyacrylamidoethylpropanesulphonic acid sold by COGNIS as COSMEDIA POLYMER® HSP 1180.

The anionic polymers are, for example, selected from acrylic acid copolymers such as the acrylic acid/ethyl acrylate/N-tertiobutylacrylamide terpolymer sold by BASF under the trade name ULTRAHOLD STRONG®, copolymers derived from crotonic acid such as vinyl acetate/vinyl tertiobutylbenzoate/crotonic acid terpolymers and crotonic acid/vinyl acetate/vinyl neododecanoate terpolymers sold by NATIONAL STARCH under the trade name RÉSINE 28-29-30, polymers derived from maleic, fumaric or itaconic acids or anhydrides with vinyl esters, vinyl ethers, vinyl halides, phenyl vinyl derivatives, acrylic acid and its esters such as the monoesterified methyl vinyl ether/maleic anhydride copolymer sold by ISP under the trade name GANTREZ® ES 425, copolymers of methacrylic acid and methyl methacrylate sold by ROHM PHARMA under the trade name EUDRAGIT® L, the copolymer of methacrylic acid and ethyl acrylate sold by BASF under the trade name LUVIMER® MAEX, the vinyl acetate/crotonic acid copolymer sold by BASF under the trade name LUVISET® CA 66 and the vinyl acetate/crotonic acid/polyethylene glycol terpolymer sold by BASF under the trade name ARISTOFLEX®.

The anionic polymers are further, for example, chosen from the monoesterified maleic methyl vinyl ether/maleic anhydride copolymer sold by ISP under the trade name GANTREZ® ES 425, copolymers of methacrylic acid and methyl methacrylate sold by ROHM PHARMA under the trade name EUDRAGIT®, the copolymer of methacrylic acid and ethyl acrylate sold by BASF under the trade name LUVIMER® MAEX, and the vinylpyrrolidone/acrylic acid/lauryl methacrylate terpolymer sold by ISP under the trade name ACRYLIDONE® LM.

It is also possible to use anionic polymers in the form of latex or pseudolatex, i.e., in the form of an aqueous dispersion of insoluble polymer particles.

The compositions can comprise at least one polymer chosen from soluble and dispersed nonionic polymers. These may include:

(1) vinylpyrrolidone homopolymers;

(2) copolymers of vinylpyrrolidone and vinyl acetate;

(3) polyalkyloxazolines, such as polyethyloxazolines sold by DOW CHEMICAL under the trade names PEOX® 50 000, PEOX® 200 000, and PEOX® 500 000;

(4) vinyl acetate homopolymers such as the product sold by HOECHST under the trade name APPRETAN® EM or the product sold by RHODIA under the trade name RHODOPAS® A 012;

(5) copolymers of vinyl acetate and an acrylic ester, such as the product sold by RHODIA under the trade name RHODOPAS® AD 310;

(6) copolymers of vinyl acetate and ethylene, such as the product sold by HOECHST under the trade name APPRETAN® TV;

(7) copolymers of vinyl acetate and a maleic ester, for example dibutyl maleate, such as the product sold by HOECHST under the trade name APPRETAN® MB EXTRA;

(8) copolymers of polyethylene and maleic anhydride;
(9) alkyl acrylate homopolymers and alkyl methacrylate homopolymers, such as the product sold by MATSUMUTO under the trade name MICROPEARL® RQ 750 or the product sold by BASF under the trade name LUHYDRAN® A 848 S;
(10) acrylic ester copolymers, such as copolymers of alkyl acrylates and alkyl methacrylates, for example, the products sold by ROHM & HAAS under the trade names PRIMAL® AC-261 K and EUDRAGIT® NE 30 D, by BASF under the trade names ACRONAL® 601, LUHYDRAN® LR 8833 or 8845, by HOECHST under the trade names APPRETAN® N 9213 or N9212;
(11) copolymers of acrylonitrile and a nonionic monomer selected, for example, from butadiene and alkyl (meth) acrylates; products sold by NIPPON ZEON under the trade name NIPOL® LX 531 8 or those sold by ROHM & HAAS under the trade name CJ 0601 8;
(12) polyurethanes, such as the products sold by ROHM & HAAS under the trade names ACRYSOL® RM 1020 or ACRYSOL® RM 2020, or products sold by DSM RESINS under the trade names URAFLEX® XP 401 UZ, URAFLEX® XP 402 UZ;
(13) copolymers of alkyl acetate and urethane, such as NATIONAL STARCH's product 8538-33;
(14) polyamides, such as the product sold by RHONE POULENC under the trade name ESTAPOR® LO 11; and
(15) chemically modified or unmodified nonionic guar gums.

Unmodified nonionic guar gums that can be used include the product sold by UNIPECTINE under the trade name VIDOGUM® GH 175 and the product sold by MEYHALL under the trade name JAGUAR® C. Modified nonionic guar gums that can be used include guar gums modified by $C_1$–$C_6$ hydroxyalkyl groups, such as hydroxymethyl, hydroxyethyl, hydroxypropyl or hydroxybutyl groups. Such guar gums are well known in the art and can, for example, be prepared by reacting the oxides of corresponding alkenes, such as propylene oxides, with guar gum to obtain a guar gum modified with hydroxypropyl groups. Examples of such nonionic guar gums optionally modified with hydroxyalkyl groups are those sold by RHODIA under the trade names JAGUAR® HP 8, JAGUAR® HP 60, JAGUAR® HP 120, JAGUAR® DC 293, and JAGUAR® HP 105, or by AQUALON under the trade name GALACTASOL® 4H4FD2.

The alkyl groups of the nonionic polymers, for example, comprise from 1 to 6 carbon atoms.

Additionally, the compositions can comprise at least one silicone. The at least one silicone that can be used may be soluble or insoluble in the compositions. For example, the at least one silicone can be chosen from polyorganosiloxanes that are insoluble in the compositions; they can be in the form of oils, waxes, resins or gums. Polyorganosiloxanes are described in more detail in Walter Noll, "Chemistry And Technology of Silicones" (Academic Press, 1968).

The silicones may be volatile or non-volatile. When they are volatile, the silicones are, for example, chosen from those with a boiling point in the range of from about 60° C. to about 260° C., and further, for example, may be chosen from:
(1) cyclic silicones comprising from 3 to 7 silicon atoms, such as 4 or 5 silicone atoms. Examples include octamethylcyclotetrasiloxane sold by UNION CARBIDE under the trade name VOLATILE SILICONE 7207 or by RHODIA under the trade name SILBIONE 70045 V2, and decamethylcyclopentasiloxane sold by UNION CARBIDE under the trade name VOLATILE SILICONE 7158, or by RHODIA under the trade name SILBIONE 70045 V 5, and mixtures thereof.

Other examples include cyclopolymers of the dimethylsiloxane/methylalkylsiloxane type such as SILICONE VOLATILE FZ 3109 sold by UNION CARBIDE, which has the following chemical structure:

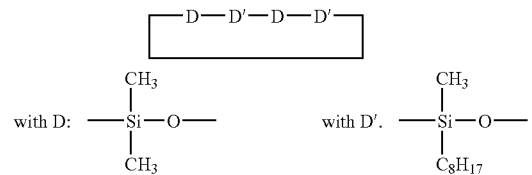

Still other examples include mixtures of cyclic silicones with organic compounds derived from silicon, such as a mixture of octamethylcyclotetrasiloxane and tetratrimethylsilylpentaerythritol (50/50) or a mixture of octamethylcyclotetrasiloxane and oxy-1,1'-(hexa-2,2,2',2',3,3'-trimethylsilyloxy) bis-neopentane; and
(2) volatile linear silicones comprising from 2 to 9 silicon atoms and with a viscosity of less than or equal to about $5 \times 10^{-6}$ m$^2$/s at 25° C. Examples include decamethyltetrasiloxane sold by TORAY SILICONE under the trade name SH 200. Silicones in this class have also been described in Todd & Byers, "Volatile silicone fluids for cosmetics," 91 Cosmetics and Toiletries, pp. 27–32 (January 76).

Non-volatile silicones including polyalkylsiloxanes, polyarylsiloxanes, polyalkylarylsiloxanes, silicone gums and resins, polyorganosiloxanes modified by organofunctional groups, and mixtures thereof may also be used.

Organomodified silicones that can be used are silicones as defined above and comprising in their structure at least one organofunctional group fixed via a hydrocarbon group. Examples of organomodified silicones include polyorganosiloxanes comprising at least one group chosen from:
(1) polyethyleneoxy and polypropyleneoxy groups optionally comprising $C_6$–$C_{24}$ alkyl groups such as dimethicone-copolyol products sold by DOW CORNING under the trade name DC 1248 or SILWET® L 722, L 7500, L 77, L 711 from UNION CARBIDE and alkyl ($C_{12}$) methicone-copolyol sold by DOW CORNING under the trade name Q2 5200;
(2) amine groups, which may or may not be substituted, such as the products sold by GENESEE under the trade name GP 4 Silicone Fluid and GP 7100 or products sold by DOW CORNING under the trade name Q2 8220 and DOW CORNING 929 or 939. For example, the substituted amine groups are chosen from $C_1$–$C_4$ aminoalkyl groups;
(3) thiol groups, such as the products sold by GENESEE under the trade name GP 72 A and GP 71;
(4) alkoxylated groups, such as the product sold by SWS SILICONES under the trade name SILICONE COPOLYMER F-755 and by GOLDSCHMIDT under the trade name ABIL WAX® 2428, 2434, and 2440;
(5) hydroxylated groups, such as polyorganosiloxanes with a hydroxyalkyl function as described in French Patent Application FR-A-85 16334;
(6) acyloxyalkyl groups, such as polyorganosiloxanes as described in U.S. Pat. No. 4,957,732;
(7) anionic groups of the carboxylic acid type, such as the products described in EP-A-0 186 507 from CHISSO CORPORATION, or of the alkylcarboxylic type such as those present in the product X-22-3701E from SHIN-ETSU; 2-hydroxyalkylsulphonate; or 2-hydroxyalkylthiosulphate, such as the products sold by GOLDSCHMIDT under the trade names ABIL® S201 and ABIL® S255; and (8) hydroxyacylamino groups, such as polyorganosiloxanes described in European Patent EP-A-0 342 834, such as those sold by DOW CORNING under the trade name Q2-8413.

It is also possible to use grafted silicones with a hydrocarbon skeleton and silicone grafts or a silicone skeleton and hydrocarbon grafts, such as the product sold by 3M under the trade name VS80.

The compositions can additionally comprise at least one oil chosen from mineral, vegetable and animal oils. Oils of vegetable origin include, for example, sweet almond oil, avocado oil, castor oil, olive oil, jojoba oil, sunflower seed oil, wheatgerm oil, sesame seed oil, peanut oil, grapeseed oil, soya oil, rapeseed oil, carthame oil, coprah oil, corn oil, hazelnut oil, shea butter, palm oil, apricot kernel oil and calophyllum oil. An oil of animal origin is, for example, perhydrosqualene. Oils of mineral origin include, for example, paraffin oil and vaseline oil.

The compositions can comprise at least one compound chosen from polyisobutenes and poly(α-olefins), chosen from those that are well known in the art.

The compositions can further comprise at least one surfactant chosen from anionic, amphoteric, nonionic and cationic surfactants. Examples of anionic surfactants that can be used alone or as a mixture include, for example, salts (such as alkaline salts, for example, sodium salts, ammonium salts, amine salts, aminoalcohol salts and magnesium salts) of the following compounds: alkyl sulphates, alkyl ether sulphates, alkylamido ether sulphates, alkylaryl polyether sulphates, monoglyceride sulphates; alkyl sulphonates, alkyl phosphates, alkylamide sulphonates, alkylaryl sulphonates, α-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates, acyl glutamates and N-acyl taurates. The alkyl or acyl radical in all of these different compounds comprise, for example, from 12 to 20 carbon atoms and the aryl radical is, for example, chosen from phenyl and benzyl groups. Anionic surfactants that can be used include, for example, salts of fatty acids such as the salts of oleic acids, ricinoleic acids, palmitic acids, stearic acids, coprah oil acids or hydrogenated coprah oil acids and acyl lactylates wherein the acyl radical comprises from 8 to 20 carbon atoms. It is also possible to use weakly anionic surfactants such as alkyl D galactoside uronic acids and their salts and polyoxyalkylenated ($C_6$–$C_{24}$)alkyl ether carboxylic acids, polyoxyalkylenated ($C_6$–$C_{24}$)alkyl aryl ether carboxylic acids, polyoxyalkylenated ($C_6$–$C_{24}$)alkyl amido ether carboxylic acids, and salts thereof, for example, those comprising from 2 to 50 ethylene oxide groups, and mixtures thereof. The anionic surfactants include, for example, alkyl sulphate and alkyl ether sulphate salts and their mixtures.

Nonionic surfactants that can be used are chosen, for example, from alcohols, alpha-diols, alkylphenols and polyethoxylated, polypropoxylated and polyglycerolated fatty acids with a fatty chain comprising from 8 to 18 carbon atoms, for example, the number of ethylene oxide or propylene oxide groups possibly ranging, for example, from 2 to 50 and the number of glycerol groups possibly ranging, for example, from 2 to 30. Nonionic surfactants may also include copolymers of ethylene oxide and propylene oxide, condensates of ethylene oxide and propylene oxide on fatty alcohols; polyethoxylated fatty amides, for example, those comprising from about 2 to about 30 mol of ethylene oxide, polyglycerolated fatty amides comprising an average of from 1 to 5 glycerol groups, and such as from 1.5 to 4 glycerol groups; polyethoxylated fatty amines, such as those comprising from about 2 to about 30 mol of ethylene oxide; fatty acid esters of oxyethylenated sorbitan comprising from about 2 to about 30 mol of ethylene oxide; fatty acid esters of saccharose, fatty acid esters of polyethylene glycol, alkylpolyglycosides, N-alkylglucamine derivatives, amine oxides such as alkyl($C_{10}$–$C_{14}$) amines or N-acylaminopropylmorpholine oxides.

Amphoteric surfactants that can be used are chosen, for example, from derivatives of aliphatic secondary and tertiary amines in which the aliphatic radical is chosen from linear and branched chains comprising from 8 to 22 carbon atoms and comprising at least one hydrosolubilizing anionic group (for example carboxylate, sulphonate, sulphate, phosphate and phosphonate); additional examples include ($C_8$–$C_{20}$)alkyl betaines, sulphobetaines, ($C_8$–$C_{20}$)alkyl amido ($C_1$–$C_6$)alkylbetaines such as cocoamidopropylbetaines or ($C_8$–$C_{20}$)alkyl amido ($C_1$–$C_6$)alkylsulphobetaines.

Among the amine derivatives, mention may be made of the products sold under the trade name MIRANOL®, as described in U.S. Pat. Nos. 2,528,378 and 2,781,354 with structures of:

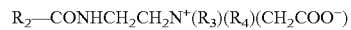

in which $R_2$ is chosen from alkyl radicals derived from an acid $R_2$—COOH present in hydrolysed coprah oil, and heptyl, nonyl and undecyl radicals; $R_3$ is a beta-hydroxyethyl group; and $R_4$ is a carboxymethyl group;

and of

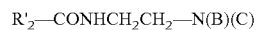

in which B represents —$CH_2CH_2OX'$, in which X' is chosen from —$CH_2CH_2$—COOH group and a hydrogen atom; C represents —$(CH_2)_z$—Y' wherein z=1 or 2 and Y' is chosen from —COOH and —$CH_2$—CHOH—$SO_3H$; and $R'_2$ is chosen from alkyl radicals of an acid $R'_2$—COOH present in coprah oil or in hydrolysed linseed oil, and alkyl radicals, such as $C_7$, $C_9$, $C_{11}$ and $C_{13}$ alkyl radicals, a $C_{17}$ alkyl radical and its iso-form, and an unsaturated $C_{17}$ radical. These compounds are classified in the CTFA dictionary (5th ed., 1993), under the denominations Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Caprylamphodipropionate, Disodium Capryloamphodipropionate, Lauroamphodipropionic acid, and Cocoamphodipropionic acid. One example is cocoamphodiacetate, sold by RHODIA CHIMIE under the trade name MIRANOL® C2M concentrate.

Cationic surfactants that can be used are chosen, for example, from salts of primary, secondary or tertiary fatty amines, optionally polyoxyalkylenated; quaternary ammonium salts; imidazoline derivatives; or amine oxides with a cationic nature. The quaternary ammonium salts are, for example, chosen from:

(1) quaternary ammonium salts with the following general formula (XV):

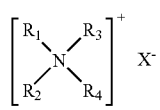
(XV)

in which the radicals $R_1$ to $R_4$, which may be identical or different, are chosen from linear and branched aliphatic radicals comprising from 1 to 30 carbon atoms and aromatic radicals such as aryl and alkylaryl. The aliphatic radicals can comprise at least one hetero atom such as oxygen, nitrogen, sulphur and halogens. The aliphatic radicals are, for example, chosen from alkyl, alkoxy, polyoxy($C_2$–$C_6$)alkylene, alkylamide, ($C_{12}$–$C_{22}$)alkylamido ($C_2$–$C_6$)alkyl, ($C_{12}$–$C_{22}$)alkylacetate and hydroxyalkyl radicals, comprising from 1 to 30 carbon atoms. $X^-$ is an anion chosen from halides, phosphates, acetates, lactates, alkyl($C_2$–$C_6$)sulphates, alkyl and alkylarylsulphonates;

(2) quaternary ammonium salts of imidazolinium, such as those with the following formula (XVI):

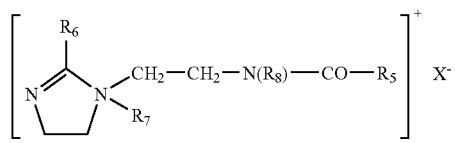
(XVI)

in which $R_5$ is chosen from alkenyl and alkyl radicals comprising from 8 to 30 carbon atoms, for example, tallow fatty acid derivatives, $R_6$ is chosen from a hydrogen atom, $C_1$–$C_4$ alkyl radicals and alkenyl and alkyl radicals comprising from 8 to 30 carbon atoms, $R_7$ is chosen from $C_1$–$C_4$ alkyl radicals, $R_8$ is chosen from a hydrogen atom, and $C_1$–$C_4$ alkyl radicals, $X^-$ is an anion chosen from halides, phosphates, acetates, lactates, alkylsulphates, alkyl- and alkylarylsulphonates. In one embodiment, $R_5$ and $R_6$ are, for example, a mixture of radicals chosen from alkenyl and alkyl radicals comprising from 12 to 21 carbon atoms, such as tallow fatty acid derivatives, $R_7$ is methyl, and $R_8$ is hydrogen. An example of such a product is sold by REWO under the trade name REWOQUAT W 75;

(3) quaternary diammonium salts with the formula (XVII):

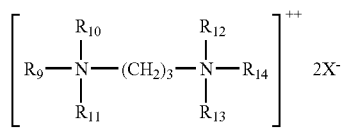
(XVII)

in which $R_9$ is chosen from aliphatic radicals comprising from 16 to 30 carbon atoms, $R_{10}$, $R_{11}$, $R_{12}$, $R_{13}$, and $R_{14}$, which may be identical or different, are chosen from hydrogen and alkyl radicals comprising from 1 to 4 carbon atoms; $X^-$ is an anion chosen from halides, acetates, phosphates, nitrates, and methylsulphates. Such quaternary diammonium salts include, for example, diammonium propanetallow dichloride;

(4) quaternary ammonium salts comprising at least one ester function, such as those with the following formula (XVIII):

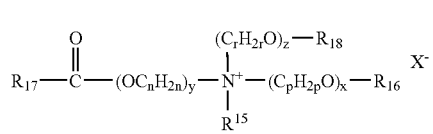
(XVIII)

In which:

$R_{15}$ is chosen from linear and branched $C_1$–$C_6$ alkyl radicals and $C_1$–$C_6$ hydroxyalkyl and dihydroxyalkyl radicals;

$R_{16}$ is chosen from hydrogen; the radical $R_{19}$—CO—, in which $R_{19}$ is chosen from linear and branched, saturated and unsaturated $C_7$–$C_{21}$ hydrocarbon radicals; and linear and branched, saturated and unsaturated $C_1$–$C_{22}$ hydrocarbon radicals;

$R_{17}$ is chosen from linear and branched, saturated and unsaturated $C_7$–$C_{21}$ hydrocarbon radicals;

$R_{18}$ is chosen from hydrogen; the radical $R_{20}$—CO—, in which $R_{20}$ is chosen from linear and branched, saturated and unsaturated $C_7$–$C_{21}$ hydrocarbon radicals; and linear and branched, saturated and unsaturated $C_1$–$C_6$ hydrocarbon radicals;

n, p, and r, which may be identical or different, are integers chosen from 2 to 6;

$X^-$ is an anion chosen from simple and complex organic and inorganic anions;

x and z, which may be identical or different, are integers chosen from 0 to 10;

y is an integer chosen from 1 to 10;

wherein the sum x+y+z is from 1 to 15; with the proviso that (1) when x=0, then $R_{16}$ is chosen from linear and branched, saturated and unsaturated $C_1$–$C_{22}$ hydrocarbon radicals; and (2) that when z=0, then $R_{18}$ is chosen from linear and branched, saturated and unsaturated $C_1$–$C_6$ hydrocarbon radicals.

In one embodiment, the $R_{15}$ alkyl radicals are linear and are chosen, for example, from methyl, ethyl, hydroxyethyl and dihydroxypropyl radicals, such as methyl and ethyl radicals., In another embodiment, the sum x+y+z is from 1 to 10. In another embodiment, when $R_{16}$ is chosen from linear and branched, saturated and unsaturated $C_1$–$C_{22}$ hydrocarbon radicals, it may, for example, contain 12 to 22 carbon atoms or 1 to 3 carbon atoms. When $R_{18}$ is chosen from linear and branched, saturated and unsaturated $C_1$–$C_6$ hydrocarbon radicals, it may, for example, contain 1 to 3 carbon atoms.

In one embodiment, $R_{17}$, $R_{19}$, and $R_{20}$, which may be identical or different, are chosen from linear and branched, saturated and unsaturated $C_{11}$–$C_{21}$ hydrocarbon radicals, such as from linear and branched, saturated and unsaturated $C_{11}$–$C_{21}$ alkyl and alkenyl radicals. In another embodiment, x and z, which may be identical or different, equal 0 or 1. For example, y equals 1. And N, p, and r, which may be identical or different, are, for example, 2 or 3 and further, for example, equal to 2.

Anion $X^-$ is chosen, for example, from halides (such as chloride, bromide and iodide) and alkylsulphates such as methylsulphate. But it is possible to use the methanesulphonate, phosphate, nitrate, tosylate, an anion derived from an organic acid such as an acetate or lactate or any other anion that is compatible with the ammonium with the ester function. For example, anion $X^-$ is chosen from chloride and methylsulphate.

In one embodiment, the ammonium salts with formula (XVIII) can be one, in which:
$R_{15}$ is chosen from methyl and ethyl radicals;
x and y equal 1;
z equals 0 or 1;
n, p, and r equal 2;
$R_{16}$ is chosen from hydrogen; the radical $R_{19}$—CO—, in which $R_{19}$ is chosen from linear and branched, saturated and unsaturated $C_{13}$–$C_{17}$ hydrocarbon radicals; methyl and ethyl radicals, and linear and branched, saturated and unsaturated $C_{14}$–$C_{22}$ hydrocarbon radicals;
$R_{17}$ is chosen from linear and branched, saturated and unsaturated $C_{13}$–$C_{17}$ hydrocarbon radicals; and
$R_{18}$ is chosen from hydrogen and radicals of $R_{20}$—CO—, in which $R_{20}$ is chosen from linear and branched, saturated and unsaturated $C_{13}$–$C_{17}$ hydrocarbon radicals.

The hydrocarbon radicals are, for example, linear. Compounds with formula (XVIII) include salts (such as chloride and methylsulphate) of diacyloxyethyl dimethyl ammonium, diacyloxyethyl hydroxyethyl methyl ammonium, monoacyloxyethyl dihydroxyethyl methyl ammonium, triacyloxyethyl methyl ammonium, monoacyloxyethyl hydroxyethyl dimethyl ammonium, and mixtures thereof. The acyl radicals, for example, comprise from 14 to 18 carbon atoms and originate from vegetable oil such as palm oil or sunflower seed oil. When the compound comprises a plurality of acyl radicals, the acryl radicals can be identical or different.

These compounds are obtained, for example, by direct esterification of triethanolamine, triisopropanolamine, alkyldiethanolamine or alkyldiisopropanolamine, optionally oxyalkylenated on fatty acids or on mixtures of fatty acids of vegetable or animal origin or by transesterification of their methyl esters. This esterification is followed by quaternization using an alkylating agent such as an alkyl halide (for example, methyl and ethyl), a dialkyl sulphate (for example, methyl and ethyl), methyl methanesulphonate, methyl para-toluenesulphonate, glycol chlorohydrin and glycerol. Compounds of this type include, for example, those sold by COGNIS under the trade name DEHYQUART, by STEPAN under the trade name STEPANQUAT, by CECA under the trade name NOXAMIUM and by REWO-WITCO under the trade name REWOQUAT WE 18.

It is also possible to use ammonium salts containing at least one ester function as described in U.S. Pat. Nos. 4,874,554 and 4,137,180. Quaternary ammonium salts of formula (XV) include, for example, tetraalkylammonium chlorides such as dialkyldimethylammonium or alkyltrimethylammonium chlorides, in which the alkyl radical comprises from 12 to 22 carbon atoms, such as behenyltrimethylammonium chlorides, distearyldimethylammonium chloride, cetyltrimethylammonium chloride, benzyldimethylstearylammonium chloride, or stearamidopropyldimethyl (myristyl acetate)ammonium chloride sold by VAN DYK under the trade name CERAPHYL 70.

In the compositions, it is, for example, possible to use mixtures of surfactants, such as mixtures of at least one anionic surfactant and at least one surfactant chosen from amphoteric and nonionic surfactants. For example, a mixture of at least one anionic surfactant and at least one amphoteric surfactant can be used.

The anionic surfactants are, for example, compounds chosen from sodium, triethanolamine and ammonium $(C_{12}$–$C_{14})$alkylsulphates, sodium $(C_{12}$–$C_{14})$alkylethersulphates oxyethylenated with about 2.2 mol of ethylene oxide, sodium cocoyl isethionate and sodium alpha$(C_{14}$–$C_{16})$olefin sulphonate and mixtures thereof with:

(1) either at least one amphoteric surfactant such as amine derivatives, for example, disodium cocoamphodipropionate or sodium cocoamphopropionate, sold, for example, by RHODIA CHIMIE under the trade name MIRANOL® C2M CONC in aqueous solution with an active content of 38% or under the trade name MIRANOL® C32;

(2) or at least one amphoteric zwitterionic-type surfactant such as alkylbetaines, for example, cocoylbetaine sold by COGNIS under the trade name DEHYTON® AB 30 in aqueous solution with a 32% active content or alkyl amidoalkylbetaines such as TEGOBETAINE® F 50, sold by GOLDSCHMIDT.

The compositions can also comprise at least one adjuvant chosen from adjuvants normally used in the cosmetic or dermatological fields, such as gelling agents and thickening agents, which may or may not be associative, of a nonionic nature such as polyurethanes, anionic, cationic or amphoteric in nature; moisturizing agents; emollients; insect repellents; thinning agents; preservatives; alkanizing and acidifying agents; fragrances; mineral and organic fillers; colorants; mineral and organic salts; vitamins; enzymes; hormones; antiparasitic agents, anti-acne agents, antiperspirant, keratolytic agents, anti-alopecia agents, and agents countering pigmentation problems.

One of ordinary skill in the art will carefully select any complementary compounds and/or their quantity so that the advantageous properties intrinsically pertaining to the composition disclosed herein are not, or are not substantially, altered by the envisaged addition. In general, complementary compounds can be present with any one compound being present in a quantity ranging from 0 to about 20% by weight relative to the total composition weight.

The compositions can be in any suitable form for topical application, such as in the form of lotion- or serum-type solutions; aqueous gels; emulsions obtained by dispersing a fatty phase in an aqueous phase (O/W) or conversely (W/O), with a liquid, semi-liquid or solid consistency such as a milk, cream of greater or lesser oiliness, or a paste. These compositions are prepared using the usual processes known in the field.

Additionally, the compositions can be used as rinse or no-rinse haircare products, such as for washing, care, conditioning, and maintaining hairstyle and for shaping keratinous fibres (such as the hair). They can be hairstyling products such as setting lotions, blow-drying lotions, fixing, and styling compositions. The lotions can be packaged in a variety of forms, such as sprays, pumps or in aerosol receptacles to ensure application of the composition in spray or mousse form. Such packaging forms are indicated, for example, when a spray or mousse for fixing or for treating the hair is required. The compositions can also be used as shampoos, rinse or no-rinse compositions, for application before or after a shampoo, a colorant, a bleach, a permanent or a straightening treatment.

The compositions can also be used as a skin care and/or hygiene product for the face or body, such as creams for protection, treatment or care of the face, hands or body, body milks for protection or for care, lotions, gels or mousses for care of the skin and the mucous membranes or for cleaning the skin.

The compositions can be used as an antisun product. The compositions can also consist of solid preparations constituting soaps or cleaning bars.

Furthermore, the compositions can be used as buccodental care products such as toothpastes or mouthwashes.

Finally, the compositions can be used as makeup products such as face creams, foundations, mascaras, eyeliners or lipsticks.

Illustrative, but non-limiting, examples are set forth below.

EXAMPLE 1

Preparation of a Wheat Starch Betainate Chloride (First Process)

(A compound of formula (I) in which Y is a starch residue, A is —$CH_2$—, $R_1=R_2=R_3$=methyl, and $X^-$ is $Cl^-$).

1.52 ml of N,N'-diisopropylcarbodiimide (9.88 mmol), 0.15 g of 4-dimethylaminopyridine (1.23 mmol), and 0.33 g of hydroxybenzotriazole (2.47 mmol) were added in succession to a solution of native wheat starch (1 g, 6.17 mmol) and N,N-dimethylglycine (0.29 g, 2.81 mmol) in 40 ml of anhydrous DMSO. The mixture was stirred in nitrogen at ambient temperature for 12 hours, then the reaction was stopped by adding 1 ml of water. The mixture was poured into 400 ml of ethanol to precipitate out the starch ester that had formed. The white precipitate was washed with acetone and vacuum-dried at ambient temperature to give 0.85 g of starch poly(N,N-dimethylglycyl)ester (yield: 74%) with a degree of substitution of 0.3.

1 ml of methyl iodide (16 mmol) was added to a solution of 0.75 g of starch poly(N,N-dimethylglycyl)ester (4 mmol) in 15 ml of anhydrous DMSO. The mixture was stirred in the dark and under nitrogen for 5 hours at ambient temperature. It was then poured into 300 ml of ethanol to precipitate out the starch betainate.

The yellow precipitate was dissolved in 100 ml of water and 50 ml of an aqueous 0.05 M NaCl solution was added. The solution was ultrafiltered through an Amicon PM10 membrane in an Amicon 8200 cell provided with an Amicon RS4 reservoir filled with 750 ml of 0.01M NaCl and pure water. Ultrafiltration was stopped when the conductivity of the filtrate was less than 10 µS. The starch betainate chloride was then recovered in the form of a white powder by freeze-drying.

0.72 g of wheat starch betainate chloride (yield: 89%) was obtained with a degree of substitution of 0.3, determined by proton NMR.

EXAMPLE 2

Preparation of a Wheat Starch Betainate Chloride from Betainyl Chloride (Second Process)

(A compound of formula (I) in which Y is a starch residue, A is —$CH_2$—, $R_1=R_2=R_3$=methyl, and $X^-$ is $Cl^-$).

1.59 ml of N,N'-diisopropylcarbodiimide (10.3 mmol), 0.156 g of 4-dimethylaminopyridine (1.284 mmol) and 0.347 g of hydroxybenzotriazole (2.57 mmol) were added in succession to a solution of native wheat starch (1.04 g, 6.42 mmol) and betainyl chloride (0.394 g, 2.57 mmol) in 40 ml of anhydrous DMSO. The mixture was stirred in nitrogen at ambient temperature for 12 hours, then the reaction was stopped by adding 1 ml of water. The mixture was then poured into 400 ml of ethanol.

The suspension was centrifuged at 1000 rpm for 12 minutes. The white precipitate was removed and washed three times with ethanol. The precipitate was then dissolved in 100 ml of water and the solution was filtered through a Sartorius membrane (pore size 8 to 3 µm).

The wheat starch betainate chloride was recovered by freeze-drying in the form of a white powder (0.88 g, yield: 75%).

EXAMPLE 3

Preparation of a Maltodextrin Betainate Chloride (A compound of formula (I) in which Y is a maltodextrin residue, A is —$CH_2$—, $R_1=R_2=R_3$=methyl, and $X^-$ is $Cl^-$).

The desired compound was prepared using the process of Example 1, while replacing the wheat starch with a maltodextrin with DPn=7 (determined by proton NMR) and using N,N-dimethylformamide as the solvent.

A maltodextrin poly(N,N-dimethylglycyl)ester was obtained (yield: 76%) with a degree of substitution of 0.3 (measured by proton NMR).

After quaternization, purification of the quaternized derivative with methyl iodide in N,N-dimethylformamide produced the desired maltodextrin betainate chloride (yield: 85%) with a degree of substitution of 0.3.

EXAMPLE 4

A conditioner was prepared comprising:

| | |
|---|---|
| maltodextrin betainate chloride from Example 3 | 0.5 g |
| behenyltrimethylammonium chloride | 1.5 g |
| mixture (80/20) of cetylstearyl alcohol and oxyethylenated cetylstearyl alcohol (33 oxyethylene moieties) | 4 g |
| water | qsp 100 g |

After applying the conditioner to the hair for two minutes then rinsing, the hair was observed to be soft and easy to disentangle.

EXAMPLE 5

A setting lotion was prepared comprising:

| | |
|---|---|
| maltodextrin betainate chloride from Example 3 | 0.5 g |
| vinylcaprolactam/vinylpyrrolidone/dimethylaminoethyl methacrylate terpolymer, 37% solution in ethanol (ADVANTAGE ® HC 37 from ISP) | 0.5 g |
| fragrance, preservative | qs |
| water | qsp 100 g |
| pH 6 | |

After applying the lotion to the hair and drying, it was observed that the hair was soft, lively, and readily styled.

What is claimed is:

1. A composition comprising, in a cosmetic or dermatologically acceptable medium, at least one compound chosen from compounds of formula (I):

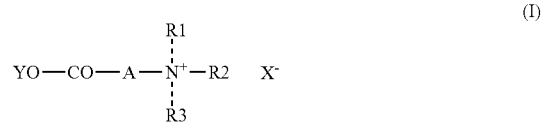

in which:

R₁, R₂, and R₃, which may be identical or different, are chosen from linear and branched, saturated and unsaturated $C_1$–$C_{30}$ hydrocarbon radicals optionally interrupted by at least one hetero atom chosen from N, O, and S, and/or optionally substituted with at least one radical selected from —OH, halogen, and $C_6$–$C_{22}$ aryl radicals;

A is chosen from linear and branched, saturated and unsaturated divalent $C_1$–$C_{22}$ hydrocarbon radicals optionally interrupted by at least one hetero atom chosen from N, O, and S, and/or optionally substituted with at least one hydroxyl radical;

X⁻ is an anion deriving from an acid chosen from mineral and organic acids; and

Y is a polysaccharide residue;

excluding the compounds of formula (I) in which Y represents a polymeric starch structure, A is —CH₂—, and R₁=R₂=R₃=—CH₃; and wherein the composition is in a form chosen from hairstyling products; shampoos, rinse and no-rinse compositions for application before or after shampoos, colorants, bleaches, permanent or straightening treatments; skin care and hygiene products for face or body; antisun products; solid preparations constituting soaps or cleaning bars; bucco-dental care products; and makeup products.

2. The composition according to claim 1, wherein the at least one compound is present in a concentration ranging from about 0.01% to about 20% by weight relative to the total weight of the composition.

3. The composition according to claim 2, wherein the at least one compound is present in a concentration ranging from about 0.05% to about 15% by weight relative to the total weight of the composition.

4. The composition according to claim 3, wherein the at least one compound is present in a concentration ranging from about 0.1% to about 10% by weight relative to the total weight of the composition.

5. The composition according to claim 1 comprising water and/or at least one organic solvent chosen from cosmetically and dermatologically accepatable organic solvents.

6. The composition according to claim 5, wherein the at least one organic solvent is present in an amount ranging from about 1% to about 98% by weight relative to the total weight of the composition.

7. The composition according to claim 5, wherein the at least one organic solvent is chosen from hydrophilic organic solvents, lipophilic organic solvents, and amphiphilic organic solvents.

8. The composition according to claim 5, wherein the at least one organic solvent is chosen from
   (a) linear and branched monoalcohols comprising from 1 to 8 carbon atoms;
   (b) polyethylene glycols comprising from about 6 to about 80 mol of ehtylene oxide;
   (c) polyols;
   (d) mono- and dialkyl isosorbides with the alkyl group comprising from 1 to 5 carbon atoms;
   (e) glycol ethers;
   (f) propylene glycol ethers; and
   (g) liquid fatty esters.

9. The composition according to claim 8, wherein in (a), the linear and branched monoalcohols are chosen from ethanol, propanol, butanol, isopropanol, and isobutanol.

10. The composition according to claim 8, wherein in (c), the polyols am chosen from propylene glycol, butylene glycol, glycerol, and sorbitol.

11. The composition according to claim 8, wherein in (d), the dialkyl isosorbides am dimethyl isosorbides.

12. The composition according to claim 8, wherein in (e), the glycol ethers am chosen from diethylene glycol monomethyl ether and diethylene glycol monoethyl ether.

13. The composition according to claim 8, wherein in (f), the propylene glycol ethers am dipropylene glycol methyl ethers.

14. The composition according to claim 8, wherein in (g), the liquid fatty esters am chosen from diisopropyl adipate, dioctyl adipate, and alkyl benzoates.

15. The composition according to claim 8, wherein in (c), the polyols am chosen from derivatives of polypropylene glycol (PPG).

16. The composition according to claim 15, wherein the derivatives of polypropylene glycol (PPG) are chosen from esters of PPG and fatty acids and esters of PPG and fatty alcohols.

17. The composition according to claim 16, wherein the esters of PPG and fatty acids and esters of PPG and fatty alcohols are chosen from PPG-23 oleyl ether and PPG-36 oleate.

18. The composition according to claim 1, further comprising at least one complementary compound chosen from monosaccharides, oligosaccharides, and polysaccharides, which may or may not be hydrolysed, and which may be modified or unmodified; amino acids, oligopeptides, peptides, and proteins, which may or may not be hydrolysed, and which may be modified or unmodified; branched and unbranched fatty alcohols and acids; waxes of animal, vegetable, and mineral origin; ceramids and pseudo-ceramids; hydroxylated organic acids; UVA-A and UV-B active sunscreens; antioxidants and free radical scavengers; chelating agents; antifungal and antibacterial agents; dandruff-regulating agents; thickening agents; cationic polymers; amphoteric polymers; soluble and dispersed anionic polymers; soluble and dispersed nonionic polymers; silicones; mineral, vegetable, and animal oils; polyisoubtenes and poly(α-olefins); anionic, amphoteric, nonionic, and cationic surfactants; gelling agents and thickening agents, which may or may not be associative, of a nonionic nature, and anionic, cationic, and amphoteric in nature; moisturizing agents; emollients; insect repellents; thinning agents; preservatives; alkalinizing and acidifying agents; fragrances; mineral and organic fillers; colourants; miner and organic salts; vitamins; enzymes; horomones; antiparasitic agents; anti-acne agents; antiperspirants; keratolytic agents; anti-alopecia agents; and agents countering pigmentation problems.

19. The composition according to claim 18, wherein the gelling agents and thickening agents, which may or may not be associative, of a nonionic nature are chosen from polyurethanes.

20. The composition according to claim 1, wherein the hairstyling products are chosen from setting lotions, blow-drying lotions, fixing and styling compositions.

21. The composition according to claim 1, wherein the skin care and hygiene products for face or body are chosen from creams for protection, treatment or care of the face, hands or the body, body milks for protection or care, lotions, gels, and mousses for care of skin and mucous membranes or for cleaning skin.

22. The composition according to claim 1, wherein the bucco-dental care products are chosen from toothpastes and mouthwashes.

23. The composition according to claim 1, wherein the makeup products are chosen from face creams, foundations, mascaras, eyeliners, and lipsticks.

24. The composition according to claim 1, wherein the composition is in a form chosen from rinse and no-rinse haircare products.

25. The composition according to claim 24, wherein the rinse and no-rinse haircare products are effective for washing, care, conditioning, maintaining a style or for shaping keratinous fibres.

26. The compositions according to claim 25, wherein the keratinous fibres are hair.

27. A process for cosmetic treatment of a keratinous support chosen from skin, scalp, hair, eyelashes, eyebrows, nails, and mucous membranes, comprising applying to said keratinous support a composition comprising, in a cosmetic or dermatologically acceptable medium, at least one compound chosen from compounds of formula (I):

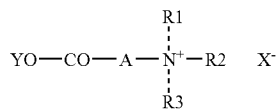

in which:

$R_1$, $R_1$, $R_2$, and $R_3$, which may be identical or different, are chosen from linear and branched, saturated and unsaturated $C_1$–$C_{30}$ hydrocarbon radicals optionally interrupted by at least one hetero atom chosen from N, O, and S, and/or optionally substituted with at least one radical selected from —OH, halogen, and $C_6$–$C_{22}$ aryl radicals;

A is chosen from linear and branched, saturated and unsaturated divalent $C_1$–$C_{22}$ hydrocarbon radicals optionally interrupted by at least one hetero atom chosen from N, O, and S, and/or optionally substituted with at least one hydroxyl radical;

$X^-$ is an anion deriving from an acid chosen from mineral and organic acids; and Y is a polysaccharide residue;

excluding the compounds of formula (I) in which Y represents a polymeric starch structure, A is —$CH_2$—, and $R_1=R_2=R_3$=—$CH_3$.

28. The composition according to claim 1, wherein the composition is a cosmetic or dermatological composition.

* * * * *

UNITED STATES PATENT AND TRADEMARK OFFICE
CERTIFICATE OF CORRECTION

PATENT NO. : 7,211,268 B2
APPLICATION NO. : 10/294685
DATED : May 1, 2007
INVENTOR(S) : Claude Dubief, Marguerite Rinaudo and Rachel Auzely-Velty It is certified that error appears in the above-identified patent and that said Letters Patent is hereby corrected as shown below:

In claim 1, column 26, lines 61-65,

"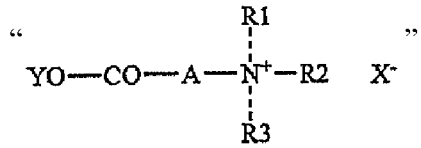"

should read

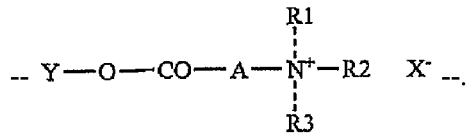.

In claim 5, column 27, line 39, "claim 1 comprising" should read --claim 1, comprising--.

In claim 8, column 27, line 55, "ehtylene" should read --ethylene--.

In claim 10, column 27, line 66, "am" should read --are--.

In claim 11, column 28, line 2, "am" should read --are--.

In claim 12, column 28, line 4, "am" should read --are--.

In claim 13, column 28, line 7, "am" should read --are--.

In claim 14, column 28, line 10, "am" should read --are--.

In claim 15, column 28, line 13, "am" should read --are--.

In claim 18, column 28, line 32, "UVA-A" should read --UV-A--.

In claim 18, column 28, line 38, "polyisoubtenes" should read --polyisobutenes--.

In claim 18, column 28, line 45, "miner" should read --mineral--.

In claim 18, column 28, line 46, "horomones" should read --hormones--.

UNITED STATES PATENT AND TRADEMARK OFFICE
CERTIFICATE OF CORRECTION

PATENT NO. : 7,211,268 B2
APPLICATION NO. : 10/294685
DATED : May 1, 2007
INVENTOR(S) : Claude Dubief, Marguerite Rinaudo and Rachel Auzely-Velty It is certified that error appears in the above-identified patent and that said Letters Patent is hereby corrected as shown below:

In claim 27, column 29, lines 18-22,

" 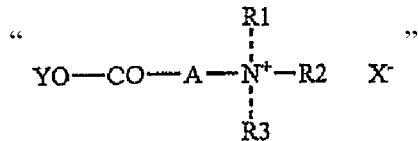 "

should read

-- 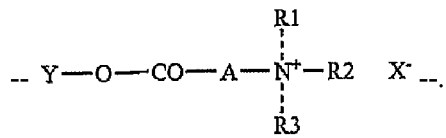 --.

In claim 27, column 30, line 2, "$R_1$, $R_1$, $R_2$," should read --$R_1$, $R_2$,--.

Signed and Sealed this

Twenty-sixth Day of June, 2007

JON W. DUDAS
*Director of the United States Patent and Trademark Office*